US00PP15657P2

(12) United States Plant Patent
Jauchen

(10) Patent No.: US PP15,657 P2
(45) Date of Patent: Mar. 15, 2005

(54) MINIATURE ROSE PLANT NAMED 'PACSIX'

(50) Latin Name: *Rosa hybrid*
Varietal Denomination: PACsix

(76) Inventor: Dan Jauchen, P.O. Box 6354, Santa Barbara, CA (US) 93160

( * ) Notice: Subject to any disclaimer, the term of this patent is extended or adjusted under 35 U.S.C. 154(b) by 26 days.

(21) Appl. No.: 10/652,697

(22) Filed: Sep. 2, 2003

(51) Int. Cl.[7] ..... A01H 5/00

(52) U.S. Cl. ..... Plt./121

(58) Field of Search ..... Plt./121, 128, 116

*Primary Examiner*—Anne Marie Grunberg
*Assistant Examiner*—June Hwu

(57) ABSTRACT

A new miniature rose plant which has abundant, pink colored flowers and attractive foliage. The variety successfully propagates from softwood cuttings and is suitable for year round production in commercial glass houses as a flowering pot plant. This new and distinct variety has shown to be uniform and stable in the resulting generations from asexual propagation.

2 Drawing Sheets

Figures 1, 2, 3, 4, 5, 6, 7, 8, 9:
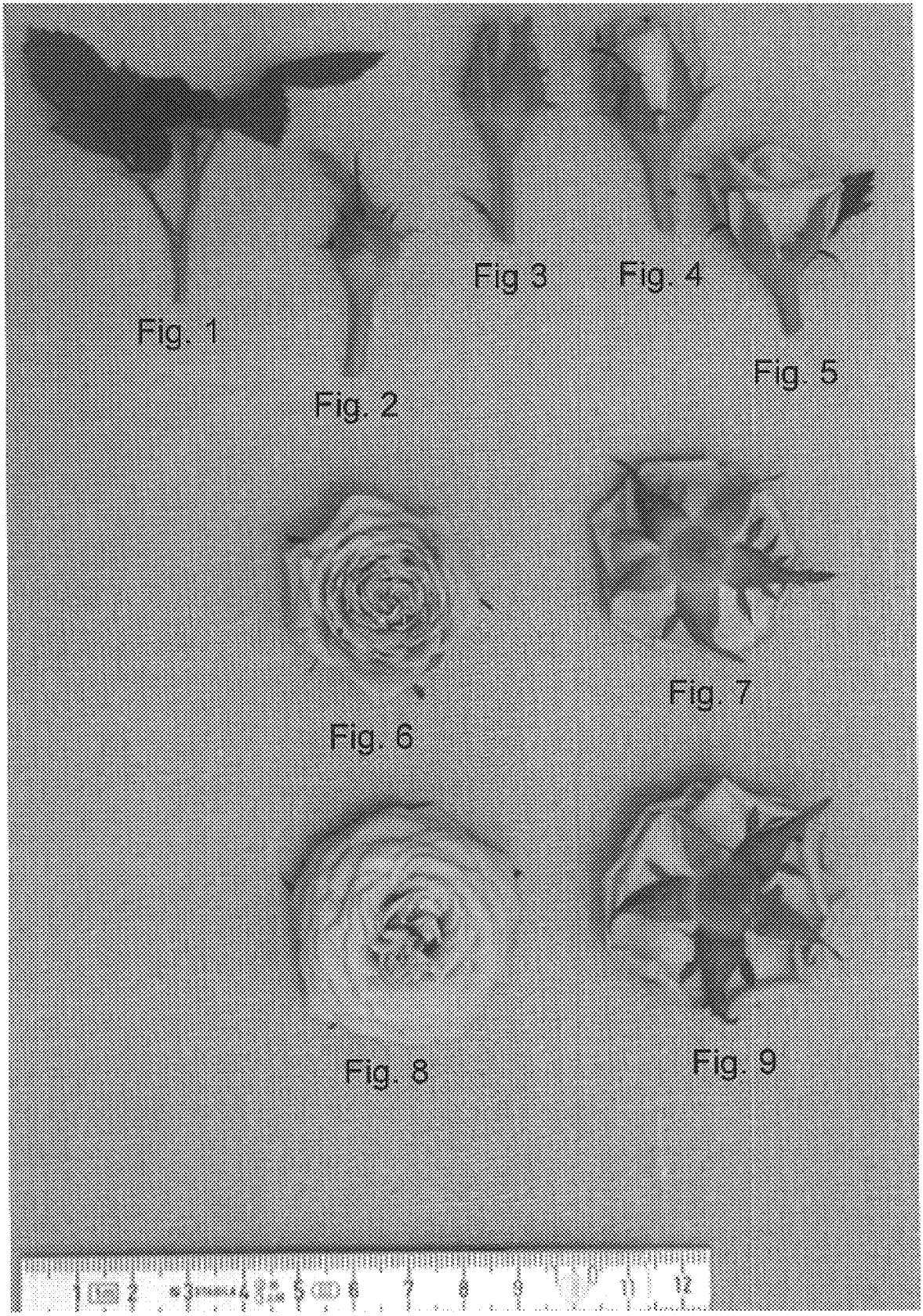

Latin name of genus and species: *Rosa hybrid* 'PACsix'.
Variety denomination: The new variety is named 'PACsix'.

BACKGROUND OF THE INVENTION

The present invention constitutes a new and distinct variety of miniature rose plant, which was developed by artificially pollinating an unnamed seedling(not patent in the US) with an unnamed seedling (not patent in the US). The two parents were crossed in the summer of 2001 and the resulting seed was sown in December 2001, in a controlled glasshouse environment. Out of these seedlings one seedling was selected, as the new variety and named 'PACsix'. The new rose may be distinguished from its seed parent, an unnamed seedling, by the following combination of characteristics:

1. The unnamed seedling has a breeding background in unnamed seedlings.
2. 'PACsix' has medium double flowers, while the unnamed seedling has big double flowers.
3. 'PACsix' has pink colored petals, while the unnamed seedling has orange petals.

The new variety may distinguished from its pollen parent, an unnamed seedling created by the same inventor, by the following combination of characteristics:

1. The unnamed seedling has a breeding background in unnamed seedlings.
2. 'PACsix' has bigger flowers and foliage as compared to the unnamed seedling.
3. 'PACsix' has pink colored petals, while the unnamed seedling has dark yellow petals.

BRIEF SUMMARY OF THE INVENTION

Initial asexual reproduction of 'PACsix' by cuttings was first done in Santa Barbara, Calif., USA. The reproduction was conducted in controlled greenhouse environments.

Have here proven that the foregoing and all after characteristics and distinctions to come true to form and are established in succeeding propagations. 'PACsix' is a low and compact miniature rose with medium vigor. The shelflife for the entire plant and the single flush, has been tested to be excellent.

The objective of the hybridization of this rose variety for commercial greenhouse culture was to create a new and distinct variety with:

1. Uniform and abundant flowers with good keepability;
2. Attractive long lasting foliage and compact growth,
3. Year round flowering under glasshouse conditions;
4. Suitability for production from softwood cuttings in pots;
5. Durable flowers and foliage which make the variety suitable for distribution in the floral industry.

This combination of qualities was not present in previously available commercial cultivars of this type and distinguish 'PACsix' from all other varieties of which we are aware.

The seeds from hybridization were planted in a controlled environment and evaluations were conducted on the resulting plants. 'PACsix' was selected by, Dan Jauchen, in his development program in Santa Barbara, Calif., USA.

BRIEF DESCRIPTIONS OF THE DRAWINGS

The accompanying color illustrations show as true as is reasonably to obtain in color photographs of this type, the typical characteristics of the buds, flowers, leaves, stems of 'PACsix'. Specifically illustrated in:

Photo sheet #1

FIG. 1 Young shoot.

FIG. 2 Bud before opening the sepals.

FIG. 3 Bud at the stage of opening the sepals.

FIG. 4 Bud at the stage of opening the petals.

FIG. 5 Flower during course of opening.

FIG. 6 Open flower—plan view—obverse.

FIG. 7 Open flower—plan view—reverse.

FIG. 8 Fully open flower—plan view—obverse.

FIG. 9 Fully open flower—plan view—reverse.

Photo sheet #2

Figures 10, 11, 12, 13, 14, 15, 16, 17, 18:
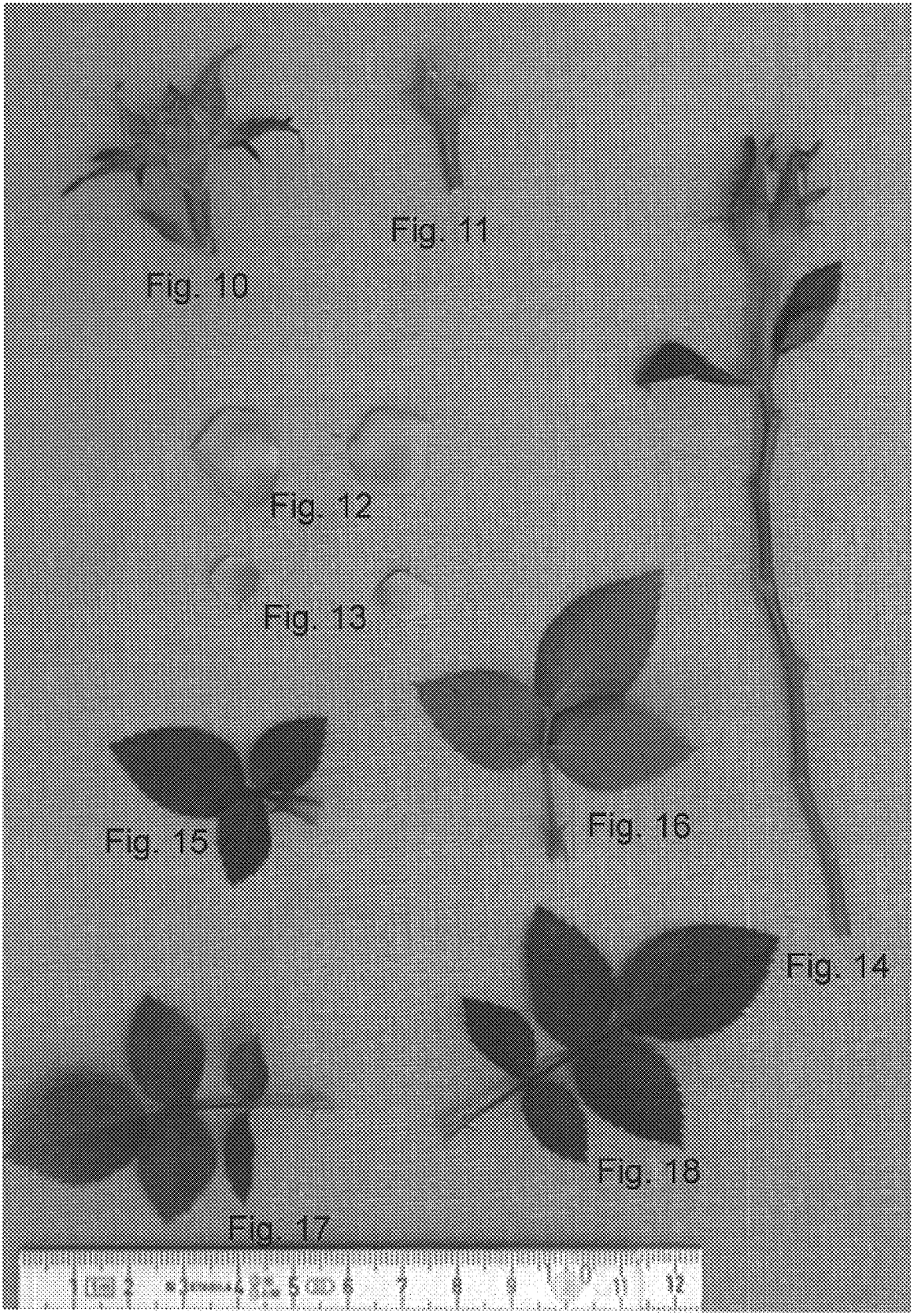

FIG. 10 Receptacle showing stamens and pistils.

FIG. 11 Receptacle showing pistils (stamens and sepals removed).

FIG. 12 Flower petals, detached—outer surface.

FIG. 13 Flower petals, detached—inner surface.

FIG. 14 Bare stem exhibiting thorns and flower attachment.

FIG. 15 Three leaflets upper side.

FIG. 16 Three leaflets reverse side.

FIG. 17 Five leaflets upper side.

FIG. 18 Five leaflets upper side.

DETAILED BOTANICAL DESCRIPTION OF THE VARIETY

The following is a detailed description of the Miniature Rose: *Rosa hybrid* 'PACsix'.

The following observations, measurements, values and comparisons describe plants grown in glass houses in Santa Barbara, Calif., USA. The age of the observed plants were 11 to 13 weeks after propagation by cuttings, and produced as flowering pot plants in container of 10.5 centimeter in diameter.

Color references are made using The Royal Horticultural Society (London, England) Colour Chart, 1995, except where common terms of color are used. For a comparison, the nearest existing rose variety is 'Ruipatros', a rose variety described and illustrated in U.S. Plant Pat. No. PP9,717.

Chart 1 details several physical characteristics of 'PACsix' and 'Ruipatros'.

CHART 1

| | 'PACsix' | 'Ruipatros' |
|---|---|---|
| Petal color, Upper surface | Orange-Red Group 33D | Red Group 38A–39B |
| Petal color, Reverse surface | Red Group 38B | Red Group 36B |
| Petal count | 55–70 | 40–65 |

Parents: Unnamed seedling. Times. Unnamed seedling.

Classification:

*Botanical.*—*Rosa hybrid.*

*Commercial.*—Miniature.

Plant:

*Plant growth.*—Moderately vigorous. Grows compact upright to bushy. When grown as 10 cm pot plant, the average height of the plant itself is 18 to 20 cm, and average width is 20 cm. When grown as a 15 cm pot plant, the average height of the plant itself is 22 to 27 cm, and average width is 30 cm. Production time is generally 11 to 13 weeks depending on average temperature, light level, and cultural practices.

Stem:

*Color.*—Young wood: Yellow-Green Group 147B. Older wood: Yellow-Green Group 147A.

*Thorns.*—Incidence: Low number of thorns. Size 2–3 mm. Color: Greyed-Yellow Group 160C. Shape: Deep concave.

*Surface.*—Young wood: Smooth. Older wood: Smooth.

*Stem diameter.*—2–4 mm.

*Internode length.*—15–20 mm.

*Numbers of internodes.*—6–8.

Plant foliage: Leaves arranged alternately, compound with 3. 5 to 7 leaflets per leaf, generally symmetrical, abundant, and flat in aspect. Stipules at petiole base.

*Quantity of leaves.*—6 to 8 per lateral branch.

*Leaf size.*—Medium 60–70 mm(l). times. 40–55 mm(w), for 5 leaflet.

*Petioles.*—Color: Greyed-Green Group 192D, with intonations of Greyed-Purple Group 182B. Margins: with stipitate glands. Length: 8–12 mm Diameter: about 0.5–1 mm.

*Stipules.*—Size: 6–7 mm. Surface: Smooth. Color: Yellow-Green Group 147B–C, with intonations of Greyed-Purple Group 182B. Margins: with stipitate glands.

*Rachis.*—Color: Greyed-Green Group 192D, with intonations of Greyed-Purple Group 182B. Margins: Margins with stipitate glands. Length: 20 to 25 mm.

*Leaflets.*—Edge: Serrated. Serration: Single. Shape: Ovate with acute apex and obtuse base. Texture: Smooth. Appearance: Dull. Size: length: 15 to 30 mm. Width: 10 to 20 mm. Color: Young foliage: Upper surface: Yellow-Green Group 147A. Lower surface: Greyed-Green Group 191B, With intonations of Greyed-Purple 182B. Color: Mature foliage: Upper surface: Yellow-Green Group 147A. Lower surface: Greyed-Green Group 191A.

Inflorescense:

*Blooming habit.*—Recurrent.

*Number of flowers.*—Generally 1 bud per flowering stem.

*Peduncle.*—Color: Yellow-Green Group 147C, Texture: Smooth. Length: 15–20 mm Strength: Upright.

*Receptacle.*—Surface: Smooth, glabrous. Shape: Funnel-shaped. Size: h: 7–9 mm w: 7–9 mm. Color: Yellow-Green Group 146C.

*Sepals.*—Quantity: 5. Shape: Narrowly Ovate w. acute tip. Texture: Leathery. Margin: Foliaceous appendages on 2 of the five sepals Appearance: Dull. Color: Upper surface: Yellow-Green Group 147B. Reverse surface: Greyed-Green Group 191A. Size: 20 mm(L), 7 mm(W).

*Buds.*—Size: 20–25 mm (h) 15–20 mm (w)upon opening. Shape: Pointed ovoid. Color: at ¼ opening, Red Group 36A.

*Flower.*—Duration. As a pot plant, flowers last form 21 to 28 days. Fragrance. Sweet honey. Size: 40–45 mm in diameter. Form: Shape of flower when viewed from the side. Up on opening: Cupped to pointed. Open flower: Flat. Color: Petals, upon opening. Upper surface: Orange-Red Group 33D, with intonations of Orange Group 29A. Reverse surface: Red Group 38B, Petals after opening: Upper surface: Red Group 37C towards the margin, Orange Group 28D towards the center. Reverse surface: Red Group 38B. Basal Petals spots: Size: 2–3 mm Color: White Group 155D General tonality: On Open flower: Third day: Red Group 38A With intonations of Orange Group 29A. Afterwards: Orange-Red Group 34A–B.

*Petals.*—Petal reflex. Outermost petals reflex backwards at opening. Fully open all petals reflex backwards. Texture. Smooth. Petal edge. Entire. Petal count. Approximately 55–70 on the average per flower. Petal size. Length 15–20 mm Width: 15–20 mm. Shape. Outer petals: Round — ovate. Inner petals: Ovate. Apex: Orbicular, Base: Obtuse to rotundate.

*Reproductive organs.*—Stamen number: Approximately 55–70 on average per flower. Pollen. Color: Yellow-Orange Group 22A, Abundance: Average. Anthers. Size: 1–2 mm Color: Yellow Group 2D, Shape: Oblong. Filaments. Size: 4–5 mm Color: Red-Purple Group 57D. Pistils number: Approximately 25–35 on average per flower. Stigmas. Location: Under in location to anthers. Color: Green-White Group 157D. Styles. Color: Green-White Group 157D. Length: 3 to 4 mm.

Development:

*Vegetation.*—Dense.

*Blooming.*—Abundant.

*Aptitude to bear fruit.*—Poor.

*Resistance to diseases.*—Above average resistance to mildew and Botrytis under normal growing conditions in Santa Barbara, Calif., USA. Hips/seeds has not been observed due to that the plant has never been grown to the stage of seed development, due to the fact, that the variety is developed for use as a flowering pot plant only.

*Winter hardiness & drought/heat tolerance.*—Due to the fact, that this variety is a potted flowering plant, developed indoor use only, the plant is not tested for winter hardiness or drought/heat tolerance.

It is claimed:

1. A new and distinct variety of rose plant of the miniature class, substantially as herein illustrated and described as a distinct and novel rose variety due to its abundant pink flowers, attractive long lasting foliage, vigorous and compact growth, year round flowering under glasshouse conditions, suitability for production from softwood cuttings in pots, and durable flowers and foliage which make the variety suitable for distribution in the floral industry.

* * * * *